United States Patent
Jian

(10) Patent No.: US 9,895,472 B2
(45) Date of Patent: Feb. 20, 2018

(54) NEGATIVE-PRESSURE WOUND THERAPY SYSTEM FOR DETECTING EXUDATE LEVEL THROUGH PHOTOELECTRONIC TOTAL INTERNAL REFLECTION

(76) Inventor: Jiqi Jian, Guangdong (CN)

( * ) Notice: Subject to any disclaimer, the term of this patent is extended or adjusted under 35 U.S.C. 154(b) by 909 days.

(21) Appl. No.: 14/349,825

(22) PCT Filed: Dec. 22, 2011

(86) PCT No.: PCT/CN2011/084447
§ 371 (c)(1),
(2), (4) Date: Apr. 25, 2014

(87) PCT Pub. No.: WO2013/063848
PCT Pub. Date: May 10, 2013

(65) Prior Publication Data
US 2014/0257209 A1    Sep. 11, 2014

(30) Foreign Application Priority Data

Oct. 31, 2011   (CN) .......................... 2011 1 0339406

(51) Int. Cl.
*A61M 1/00* (2006.01)
*G01F 23/284* (2006.01)
(Continued)

(52) U.S. Cl.
CPC ........ *A61M 1/0025* (2014.02); *A61M 1/0001* (2013.01); *G01F 23/284* (2013.01);
(Continued)

(58) Field of Classification Search
CPC ........ A61M 1/00; A61M 13/02; A61M 27/00; A61F 13/00; A61B 17/50
See application file for complete search history.

(56) References Cited

U.S. PATENT DOCUMENTS

| 4,788,444 A | 11/1988 | Williams |
| 6,012,795 A | 1/2000 | Saito et al. |
| 8,257,328 B2 * | 9/2012 | Augustine ........... A61M 1/0049 604/313 |

FOREIGN PATENT DOCUMENTS

| CN | 1952623 | * | 1/2006 |
| CN | 1952623 A | | 4/2007 |

(Continued)

OTHER PUBLICATIONS

International Search Report for PCT/CN2011/084447 dated Jul. 12, 2012.

*Primary Examiner* — Tatyana Zalukaeva
*Assistant Examiner* — Ilya Treyger
(74) *Attorney, Agent, or Firm* — RatnerPrestia

(57) ABSTRACT

A negative pressure wound therapy system with exudate level detection through photoelectric total internal reflection, includes: a negative pressure wound therapy device; a fluid collection canister for collecting exudates, where a side wall of the fluid collection canister protrudes outward to form a protrusion, an angle θ formed by two planes where two opposite sides of the protrusion are located respectively is greater than 97.2 degrees and smaller than 180 degrees; and at least one detecting module, including: a transmitting unit arranged at one side of the protrusion; a receiving unit arranged at the other side of the protrusion; and a detection control unit, adapted to determine, according to a determination of whether the receiving unit receives the electromagnetic wave or ultrasonic wave signal transmitted by the transmitting unit, whether there exit exudates where the detecting unit is located.

9 Claims, 3 Drawing Sheets

(51) Int. Cl.
  *G01F 23/292*  (2006.01)
  *G01F 23/296*  (2006.01)
  *A61M 13/00*  (2006.01)
  *A61M 27/00*  (2006.01)
  *A61F 13/00*  (2006.01)
  *A61B 17/50*  (2006.01)

(52) U.S. Cl.
  CPC .......... *G01F 23/292* (2013.01); *G01F 23/296* (2013.01); *A61M 1/0088* (2013.01); *A61M 2205/18* (2013.01); *A61M 2205/3317* (2013.01); *A61M 2205/3375* (2013.01); *A61M 2205/3389* (2013.01); *A61M 2205/702* (2013.01)

(56) References Cited

FOREIGN PATENT DOCUMENTS

| CN | 101564937 A | 10/2009 |
| CN | 101884575 A | 11/2010 |
| CN | 101940804 A | 1/2011 |
| CN | 202355683 U | 8/2012 |

\* cited by examiner

NEGATIVE-PRESSURE WOUND THERAPY SYSTEM FOR DETECTING EXUDATE LEVEL THROUGH PHOTOELECTRONIC TOTAL INTERNAL REFLECTION

The present application is the U.S. National Phase Application of International Application PCT/CN2011/084447, entitled "NEGATIVE-PRESSURE WOUND THERAPY SYSTEM FOR DETECTING EXUDATE LEVEL THROUGH PHOTOELECTRONIC TOTAL INTERNAL REFLECTION", filed on Dec. 22, 2011, which claims the priority to Chinese Patent Application No. 201110339406.9, entitled "NEGATIVE-PRESSURE WOUND THERAPY SYSTEM FOR DETECTING EXUDATE LEVEL THROUGH PHOTOELECTRONIC TOTAL INTERNAL REFLECTION", filed on Oct. 31, 2011 with the Chinese State Intellectual Property Office, both of which are incorporated herein by reference in their entirety.

FIELD

The present disclosure relates to the technical field of negative pressure wound therapy devices, and in particular to a negative pressure wound therapy system with exudate level detection through photoelectric total internal reflection.

BACKGROUND

The principle of negative pressure wound therapy devices (NPWT) is to promote wound healing by applying a negative pressure on a wound area. The clinical practice of the United States in the last decade shows that the device is very effective in healing acute and chronic wounds.

Generally, a negative pressure wound therapy system includes a negative pressure wound therapy device, a wound kit and a container for collecting wound exudates (refers to a fluid collection canister). The wound kit is adapted to enclose a wound and create a negative pressure space. The negative pressure wound therapy device, including a negative pressure source and a controller, is adapted to create a desirable negative pressure space for the wound. FIG. 1 shows a common negative pressure wound therapy device, where a negative pressure wound therapy device 8 is schematically shown within the dashed box; the skin tissue around the wound is indicated by the reference number 1; the wound area is covered by a wound filler 2; a wound enclosure 3 is arranged above the wound filler 2 to enclose the wound, where the wound filler 2 is in communication with a fluid collection canister 5 via a catheter 4, hence the exudates from the wound may be guided into the fluid collection canister 5 which is adapted to collect the exudates from the wound. The other end of the fluid collection canister 5 is connected to a negative pressure source 6 which may provide a negative pressure for powering the flowing of the wound exudates into the fluid collection canister 5; the negative pressure source 6 is connected to a controller 7 which may control the negative pressure source 6. Generally, the device is characterized in that the fluid collection canister is designed to be matched with the device, i.e., the fluid collection canister is designed in various shapes, such as rectangle, to fit with the device closely. In the practical use of negative pressure wound therapy system, the exudates are required not to flow back into the negative pressure wound therapy device in a case that the fluid collection canister is full of the wound exudates, and the fluid collection canister is required to be replaced timely. Generally, the medical staff or patient needs to observe directly whether the fluid collection canister is full of fluid, which is inconvenient.

SUMMARY

It is to provide a negative pressure wound therapy system with exudate level detection through photoelectric total internal reflection, which may detect an exudate level in a fluid collection canister to facilitate the use for the medical stuff and patients.

In view of this, the negative pressure wound therapy system with exudate level detection through photoelectric total internal reflection includes:

a negative pressure wound therapy device including a negative pressure source and a controller;

a fluid collection canister for collecting exudates, where one side wall of the fluid collection canister protrudes outward to form a protrusion, where an angle θ formed by two planes where two opposite sides of the protrusion are located respectively is greater than 97.2 degrees and smaller than 180 degrees; and at least one detecting module, including:

a transmitting unit, arranged at one side of the protrusion, where the transmitting unit is adapted to transmit an electromagnetic wave or ultrasonic wave signal to the fluid collection canister;

a receiving unit, arranged at the other side of the protrusion, where the receiving unit is adapted to receive the electromagnetic wave or ultrasonic wave signal refracted by the fluid collection canister; and a detection control unit, adapted to determine, according to a determination of whether the receiving unit receives the electromagnetic wave or ultrasonic wave signal, whether there exit exudates where the detecting unit is located.

Preferably, the detection control unit determines that there is no exudate where the detecting module is located in a case that the receiving unit receives the electromagnetic wave or ultrasonic wave signal refracted by the fluid collection canister, where the detection control unit determines that there exist exudates where the detecting module is located in a case that the receiving unit receives any signal due to a total internal reflection of the fluid collection canister.

Preferably, the electromagnetic wave is infrared ray, visible light or ultraviolet ray.

Preferably, a plurality of grades for the exudate level are set in the fluid collection canister, and each grade corresponds to one detecting module.

Preferably, the system further includes an alarming apparatus, where in a case that the detection control unit of the detecting module at a top grade for the exudate level determines according to a determination of whether the receiving unit receives the electromagnetic wave or ultrasonic wave signal that there exist exudates at the top grade for the exudate level, it is determined that the collection canister is full of wound exudates, and a warning trigger signal is sent to the alarming apparatus, and the alarming apparatus sends out an alarming signal.

Preferably, the detection control unit controls an intensity of the electromagnetic wave or ultrasonic wave transmitted by the transmitting unit.

Preferably, detection control unit controls a coding rule for the electromagnetic wave or ultrasonic wave transmitted by the transmitting unit, and determines whether a received code is valid and controls the receiving unit whether or not to perform receiving.

Preferably, the amount of the detecting module is from 2 to 10.

Preferably, the system further includes a display unit, where the display unit is arranged in the negative pressure wound therapy system and connected to the detection control unit to display the grades for the exudate level in the fluid collection canister.

Preferably, θ is 100 degrees.

In this disclosure, a protrusion is formed at a side of the fluid collection canister, and an angle formed by the planes where the two side walls of the protrusion are located respectively is designed reasonably. Hence, total internal reflection of the electromagnetic wave or ultrasonic wave signal(s) transmitted by the transmitting unit of the detecting module arranged at one side of the protrusion occurs in a case that there exist exudates where the detecting module is located, and then a receiving unit arranged at the other side of the protrusion may not receive any signal; while in a case that there is no exudate where the detecting module is located, the receiving unit may receive the signal refracted by the fluid collection canister. The detection control unit may determine whether there exist exudates where the detecting module of the fluid collection canister is located according to a determination of whether the receiving unit receives the signal and accordingly detect the wound exudate level in the fluid collection canister, such that the medical staff and patient may learn the volume of the exudates in the fluid collection canister timely and learn whether the fluid collection canister is full of the exudates timely, thereby avoid the case that the exudates flows back into the negative pressure wound therapy device and facilitating the usage of the device.

DETAILED DESCRIPTION

The general idea of the disclosure is that the refractive index for electromagnetic or ultrasonic wave passing a certain position of a fluid collection canister depends on whether there exist exudates in the position of the fluid collection canister. In a case that there is no exudate in the fluid collection canister, the electromagnetic or ultrasonic wave signal refracted by the fluid collection canister may be received by a receiving unit; in a case that there exists exudates in the fluid collection canister, the total internal reflection of the transmitted electromagnetic or ultrasonic wave signal occurs due to the reflection by the fluid collection canister and the exudates in the fluid collection canister, and then the receiving unit may not receive the signal; hence a liquid volume in the fluid collection canister may be detected. Therefore, on the basis of the existing negative pressure wound therapy system, at least one detecting module is arranged additionally, where the detecting module includes a transmitting unit, a receiving unit and a detection control unit. The transmitting unit transmits electromagnetic wave or ultrasonic wave signal(s) to the fluid collection canister; the electromagnetic wave or ultrasonic wave signal refracted by the fluid collection canister may be received, or no signal may be received due to a total internal reflection in the fluid collection canister; therefore, the detection control module may perform determination according to a determination of whether the receiving unit receives the electromagnetic wave or ultrasonic wave signal, and in a case that the receiving unit does not receive the electromagnetic wave or ultrasonic wave signal, it may be determined that the total internal reflection of the electromagnetic wave or ultrasonic wave transmitted by the transmitting unit occurs due to the reflection by a canister wall of the fluid collection canister and there exist wound exudates where the detecting module is located.

The disclosure may be specified in the following in conjunction with drawings and a preferable embodiment.

Figure 1:
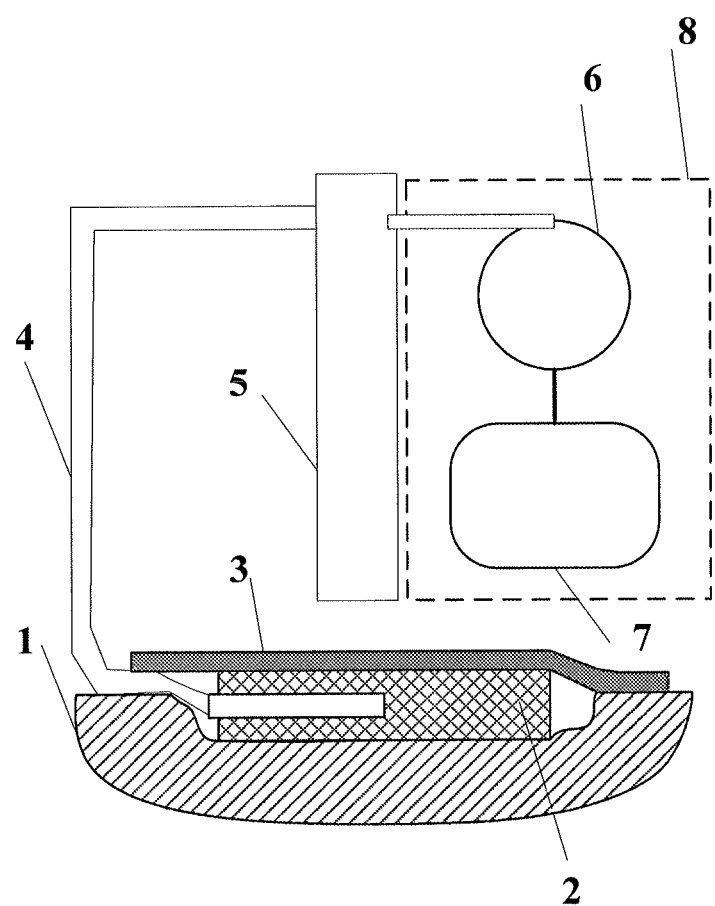
FIG. 1 is a schematic structure diagram of an existing negative pressure wound therapy system.
Figure 2:
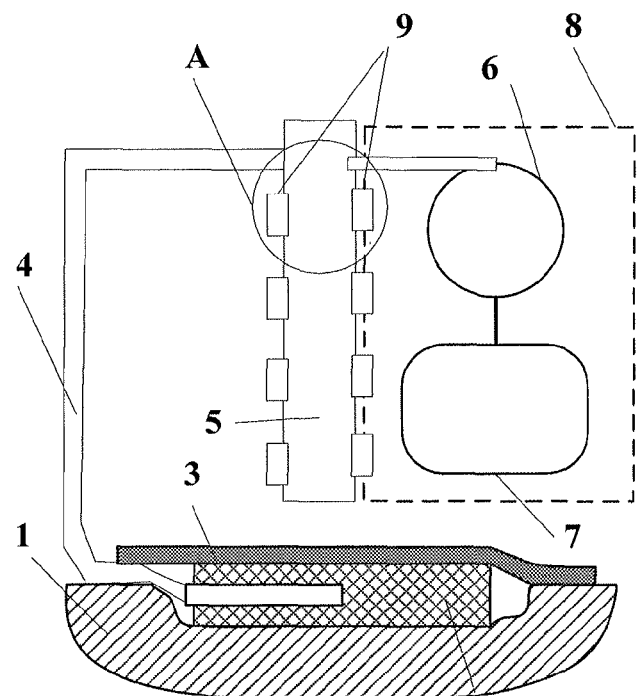
FIG. 2 is a schematic structure diagram of a negative pressure wound therapy system with exudate level detection through photoelectric total internal reflection provided according to a preferable embodiment of the disclosure.
Figure 3:
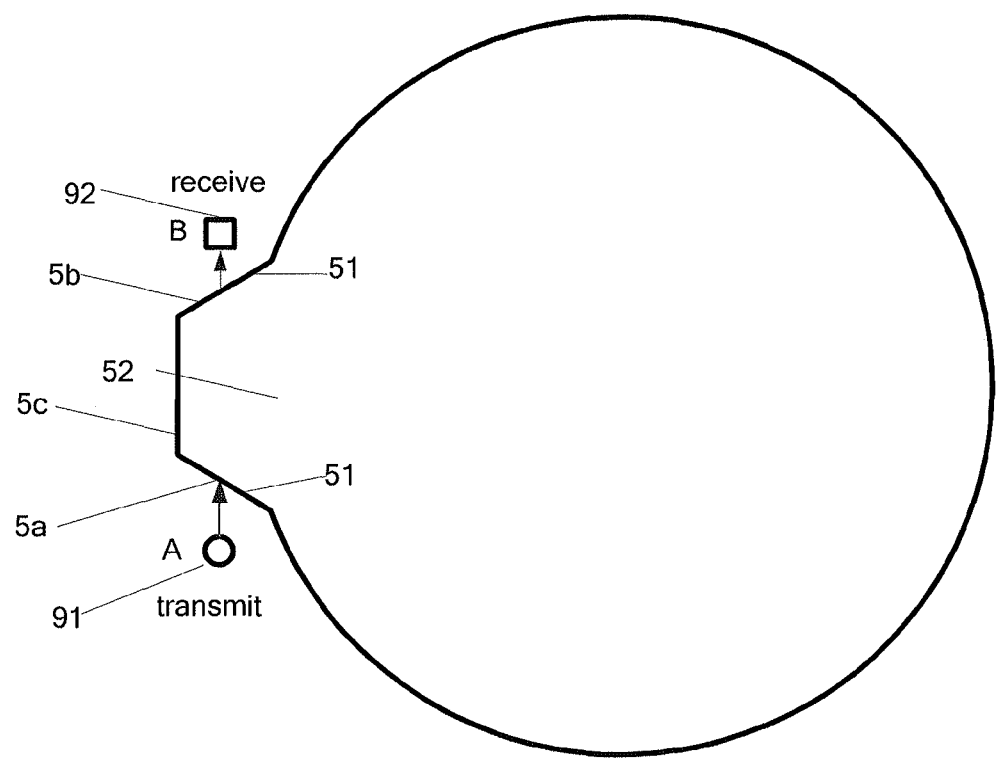
FIG. 3 is a top sectional view of the fluid collection canister shown in FIG. 2 which shows a light path in part A of FIG. 2.

As shown in FIG. 2, the negative pressure wound therapy system with exudate level detection through photoelectric total internal reflection provided according to the embodiment of the disclosure includes:

a fluid collection canister 5, including a protrusion located throughout a side wall of the fluid collection canister in the vertical direction, where the protrusion is formed in a way that the side wall of the fluid collection canister protrudes outward at a position throughout the length of the side wall, an angle θ formed by the planes where both sides 5a and 5b of the protrusion are located respectively is 100 degrees, and the fluid collection canister is adapted to collect wound exudates, as shown in FIG. 3;

a negative pressure wound therapy device 8, including a negative pressure source 6 and a controller 7;

a wound kit, adapted to fill and enclose the wound, including a wound filler 2 and a wound enclosure 3, where the wound filler 2 is in communication with the fluid collection canister 5 via a catheter 4; and four detecting modules 9, arranged along the vertical direction at the protrusion of the fluid collection canister 5, where each detecting module 9 corresponds to a grade for the exudate level, and the detecting module 9 includes:

a transmitting unit 91, adapted to transmit an electromagnetic wave or ultrasonic wave signal to the fluid collection canister, where the transmitting unit 91 is arranged at one side 5a of the protrusion;

a receiving unit 92, adapted to receive the electromagnetic wave or ultrasonic wave signal refracted through the fluid collection canister, or fail to receive any signal due to a total internal reflection in the fluid collection canister, where the receiving unit is arranged at the other side 5b of the fluid collection canister opposite to the transmitting unit 91 in a way that the receiving unit may receive the electromagnetic wave or ultrasonic wave signal passed through and refracted by the protrusion in a case that there is no exudate where the receiving unit is located; and a detection control unit, adapted to determine that there is no exudate where the detecting module is located in a case that the receiving unit receives the electromagnetic wave or ultrasonic wave signal refracted by the fluid collection canister, or to determine that there exist exudates where the detecting module is located in a case that the receiving unit receives any signal due to the total internal reflection in the fluid collection canister.

The electromagnetic wave adopted in this embodiment is infrared ray, and alternatively visible light and ultraviolet ray may be adopted.

The four grades for exudate level may be set in the fluid collection canister, and each grade corresponds to one detecting module 9. The determination whether there exist exudates where the detecting module 9 is located depends on whether the receiving unit of the detecting unit 9 receives infrared ray signal(s), and then the level of the exudates in the fluid collection canister may be determined according to the number of the receiving units which receive the infrared ray signal(s).

An alarming apparatus (not shown in FIG. 2) is further provided according to the embodiment. The detection control unit of the detecting module at a top grade for the exudate level performs determination according to whether the receiving unit receives the electromagnetic wave or ultrasonic wave signal(s) refracted by the fluid collection canister or does not receive any signal due to the total internal reflection in the fluid collection canister. If the receiving unit does not receive any signal, it may be determined that the collection canister is full of wound exudates, and then a warning trigger signal may be sent to the alarming apparatus. The alarming apparatus may send out an alarming signal to remind the medical staff or patient to replace the fluid collection canister timely.

The detection control unit controls an intensity of the electromagnetic wave or ultrasonic wave transmitted by the transmitting unit such that the electromagnetic wave or ultrasonic wave may be intense enough to be distinguished from other interference light and to be received by the receiving unit, thereby improving the sensitivity of detection.

The detection control unit controls a coding rule for the electromagnetic wave or ultrasonic wave transmitted by the transmitting unit, and determines whether a received code is valid and controls the receiving unit whether or not to perform receiving.

The amount of the detecting unit may be 2, 3, 5, 6, 7, 8, 9 or 10 as needed.

A display unit (not shown in FIG. 2), which is arranged in the negative pressure wound therapy device, is further provided according to the embodiment of the disclosure, where the display unit is connected to the detection control unit to display the grades for the exudate level in the fluid collection canister, to make the device easy to use.

The principle of the disclosure may be specified in the following.

FIG. 3 is a is a top sectional view of the fluid collection canister provided according to this embodiment and shows a light path in part A of FIG. 2. In a case that there is no exudate in the fluid collection canister, the transmitting unit 91 transmits an infrared ray; the infrared ray may enter into an internal area 52 of the fluid collection canister after being passed through and refracted by one side of the side wall 51 of the fluid collection canister, and then the infrared ray may pass out the other side of the side wall 51 of the fluid collection canister; and the receiving unit 92 receives the infrared ray passed through and refracted by the fluid collection canister. In a case that there exist fluid in the fluid collection canister, the infrared ray transmitted by the transmitting unit 91 may enter into the internal area 52 of the fluid collection canister after being passed through and refracted by one side of the side wall 51 of the fluid collection canister, and the total internal reflection of the infrared ray occurs due to the reflection by the other side of the side wall 51 of the fluid collection canister, and then the receiving unit 92 may not receive the infrared ray.

Figure 4:
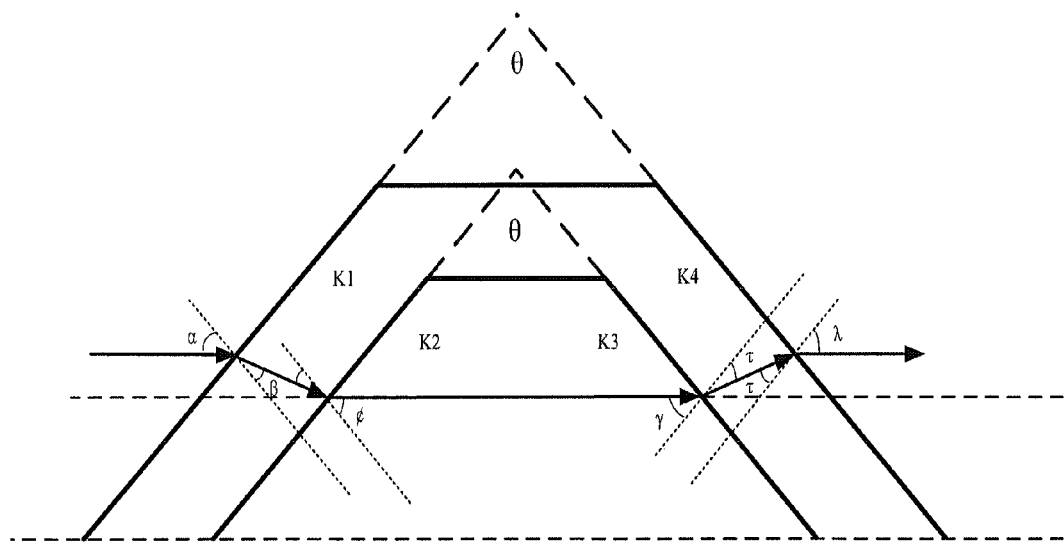
FIG. 4 is a schematic diagram showing a light path in a case that there is no exudate in a certain place of the fluid collection canister.

FIG. 4 is a schematic diagram showing a light path in a case that there is no exudate in a certain place of the fluid collection canister. A further analysis of the light path of infrared ray in a case that there is no exudate in the fluid collection canister where the transmitting unit and the receiving unit are located is as follows.

It is assumed that K1 is an outer surface of the protrusion of the fluid collection canister 5 where the infrared ray is incident, K2 is an inner surface of a shell of the fluid collection canister 5 where the infrared ray is incident, K3 is an inner surface of the protrusion of the fluid collection canister 5 where the infrared ray goes out, and K4 is an outer surface of the protrusion of the fluid collection canister 5 where the infrared ray goes out; $\alpha$ is an angle formed by a normal and the infrared ray coming into K1, $\beta$ is an angle formed by the normal and the infrared ray coming into K2, $\varphi$ is an angle formed by the normal and the infrared ray going out from K2, 7 is an angle formed by a normal and the infrared ray comes into K3, $\tau$ is an angle formed by the normal and the infrared ray going out from K3, and $\lambda$ is an angle formed by the normal and the infrared ray going out from K4. $\theta$ is an angle formed by the planes where the two opposite sides of the protrusion are located respectively, where $\theta$ is 100 degrees. It is assumed that h is a thickness of the side wall of the fluid collection canister.

It is assumed that L1 is a refractive index of the canister wall of the fluid collection canister, and the refractive index of air is approx. 1. From the refraction law, sin $\alpha \approx$ L1 sin $\beta$=sin $\varphi$, hence $\alpha \approx \varphi$, in the same way, $\lambda=\gamma$. Due to symmetry, $\varphi=\lambda$, hence $\alpha=\gamma$.

Therefore, in the case that the angle formed by the planes where the two opposite sides of the protrusion are located is 100 degrees, the protrusion may cooperate with the detecting module to detect the exudate level. A front end 5c of the protrusion is a plane, which is parallel to the vertical cross-section of the fluid collection canister. Therefore, infrared ray S11 coming into the outer surface of the canister wall of the fluid collection canister is parallel to infrared ray S13 going out from the outer surface of the canister wall of the fluid collection canister.

Therefore, as shown in FIG. 4, the receiving and the transmitting units of each detecting module are arranged in a same horizon line, and the receiving unit may receive the refracted infrared ray, hence it may be determined that there is no exudate where the detecting module is located.

Figure 5:
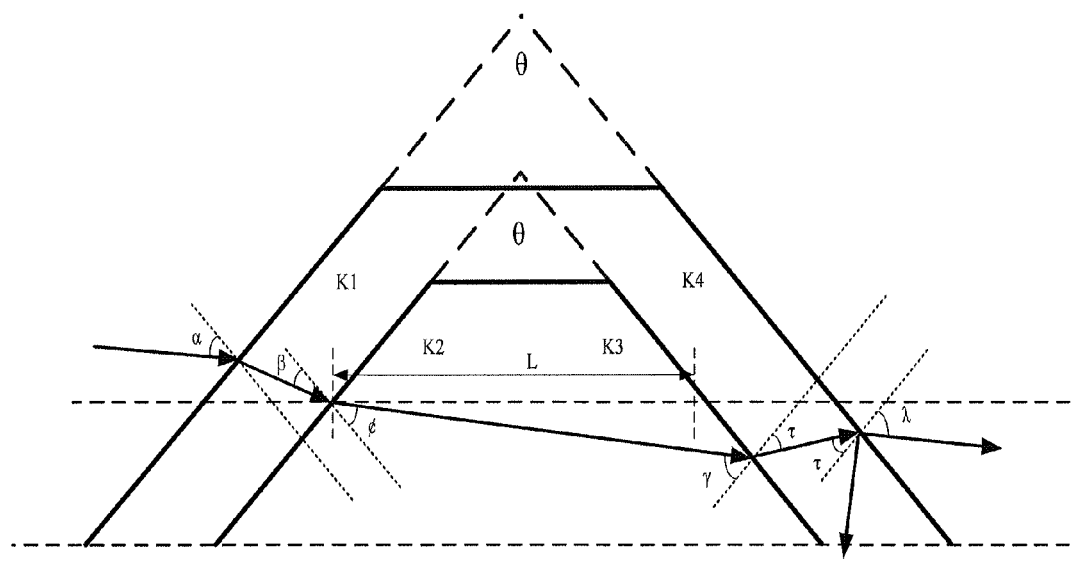
FIG. 5 is a schematic diagram showing a light path in a case that there exist exudates in a certain place of the fluid collection canister.

FIG. 5 is a schematic diagram showing a light path in a case that there is no exudate in a certain place of the fluid collection canister. A further analysis of the light path of infrared ray in a case that there is no exudate in the fluid collection canister where the transmitting unit and the receiving unit are located is as follows.

It is assumed that K1 is an outer surface of the protrusion of the fluid collection canister 5 where the infrared ray is incident, K2 is an inner surface of the protrusion of the fluid collection canister 5 where the infrared ray comes into, K3 is an inner surface of the protrusion of the fluid collection canister 5 where the infrared ray goes out, and K4 is an outer surface of the protrusion of the fluid collection canister 5 where the infrared ray goes out; and $\alpha$ is an angle formed by a normal and an infrared ray coming into K1, $\beta$ is an angle formed by the normal and the infrared ray coming into K2, $\varphi$ is an angle formed by the normal and the infrared ray going out from K2, γ is an angle formed by a normal and the infrared ray comes into K3, τ is an angle formed by the normal and the infrared ray going out from K3, and λ is an angle formed by the normal and the infrared ray going out from K4; θ is an angle formed by the planes where the two opposite sides of the protrusion are located respectively, where θ is 100 degrees. It is assumed that h is a thickness of the side wall of the fluid collection canister.

$$\theta = \gamma + \varphi \tag{1}$$

The refractive index of the canister wall is assumed to be $L_1$, the refractive index of the exudates (transparent) is $L_2$ (in the calculation the actual refractive index takes the value of 1.33, which is the refractive index of water), and the refractive index of air is 1 (approx. 1.0003 in practice).

$$\arcsin(1/L_2) = 48.6 \text{ degrees}$$

From the equation of refractive index:

$$\sin \alpha = L_1 \sin \beta = L_2 \sin \varphi \tag{2}$$

$$\sin \lambda = L_1 \sin \tau = L_2 \sin \gamma \tag{3}$$

In the four surfaces, a total internal reflection may not occur at K1 and K3 (a total internal reflection occurs only in a case that the light is transmitted from a medium of small refractive index to a medium of large refractive index).

In addition, the total reflection may not occur at K2 (according to equation 2, necessarily there exist a φ from which the light may come into the exudates. Obviously, since the light is incident from the air to the canister wall, the incident angle of the light from the canister wall to the exudates is restricted to be not wide enough for total internal reflection).

Only the possibility of a total internal reflection occurring at K4 may be discussed.

As shown in FIG. 5, the premise of occurring a total internal reflection with an incident angle τ is:

$$L_1 \sin \tau >= 1 \tag{4}$$

According to equation 3:

$$L_1 \sin \tau = L_2 \sin \gamma >= 1 \tag{5}$$

$$\gamma >= \arcsin\left(\frac{1}{L_2}\right) \tag{6}$$

where the arcsin $(1/L_2)$ is a critical angle for the exudates as the medium.

According to equation 2:

$$L_2 \sin \phi = \sin \alpha <= 1 \tag{7}$$

$$\phi <= \arcsin\left(\frac{1}{L_2}\right) \tag{8}$$

Obviously, in a case that $\theta = 2 \arcsin(1/L_2) = 97.2$, due to equation 8:

$$\gamma >= \arcsin\left(\frac{1}{L_2}\right)$$

Once θ is greater than 97.2 degrees and smaller than 180 degrees, it is qualified for the case that the total internal reflection may occur at K4. In that case, regardless of what the incident angle α is, the light may not reach the other side of K4.

In summary, if the total internal reflection of the incident light is required to occur at K4, a corresponding structure design is needed, i.e., arranging a protrusion, where the angle θ formed by the two planes where the two sides of the protrusion are located respectively may be greater than 97.2 degrees and smaller than 180 degrees.

In this embodiment, the angle θ formed by the two planes where the two sides of the protrusion of the fluid collection canister are located respectively is designed to be 100 degrees. As shown in FIG. 5, the receiving unit does not receive any signal due to the total internal reflection in the fluid collection canister, hence it may be determined that there exist wound exudates where the receiving unit is located in the fluid collection canister.

In this embodiment, by making use of the feature set forth above and setting the position(s) of the receiving unit(s), the receiving unit(s) may receive a refracted light in a case that there is no exudate in the fluid collection canister, and may not receive the refracted light in a case that there exist exudates in the fluid collection canister.

In the negative pressure wound therapy system with exudate level detection through photoelectric total internal reflection according the disclosure, the usage of the negative pressure wound therapy system may be more intellectualized, and the fluid level in the fluid collection canister of the negative pressure wound therapy device may be measured, and the volume of exudates may be measured accordingly.

In this embodiment, θ is 100 degrees; in other embodiments, θ may be any value from 97.2 degrees to 180 degrees. In this embodiment, the front end of the protrusion is a plane; in other embodiments, the front end of the protrusion may be a camber or other irregular shape, by which the same effect may be achieved.

Detailed description is set forth above, and the principle and implementation of the disclosure are described in conjunction with embodiments. The embodiments are only to help better understanding of the method and the concept of the disclosure. It should be noted that modifications and improvements may be made by those skilled in the art within the principle of the disclosure and those modifications and improvements fall into the scope of the claims of the disclosure.

The invention claimed is:

1. A negative pressure wound therapy system with exudate level detection through photoelectric total internal reflection, comprising:
    a negative pressure wound therapy device comprising a negative pressure source and a controller;
    a fluid collection canister for collecting exudates, wherein a side wall of the fluid collection canister protrudes outward to form a protrusion throughout the side wall of the fluid collection canister in a vertical direction, the protrusion comprises two side walls where two opposite sides of the protrusion are located respectively an angle θ formed by the two side walls of the protrusion is greater than 97.2 degrees and smaller than 180 degrees; and
    at least one detecting module, comprising:
    a transmitting unit arranged at one side of the protrusion, wherein the transmitting unit is adapted to transmit an electromagnetic wave or ultrasonic wave signal to the fluid collection canister;
    a receiving unit arranged at the other side of the protrusion, wherein the receiving unit is adapted to receive the electromagnetic wave or ultrasonic wave signal refracted by the fluid collection canister; and a detection control unit, adapted to determine, according to a determination of whether the receiving unit receives the electromagnetic wave or ultrasonic wave signal, whether there exit exudates where the detecting unit is located;

wherein the transmitting unit and the receiving unit are arranged at a same horizontal level; and wherein the detection control unit is adapted to determine that there is no exudate where the detecting module is located in a case that the receiving unit receives the electromagnetic wave or ultrasonic wave signal refracted by the fluid collection canister, and is adapted to determine that there exist exudates where the detecting module is located in a case that the receiving unit does not receive any signal due to a total internal reflection of the fluid collection canister.

2. The negative pressure wound therapy system with exudate level detection through photoelectric total internal reflection according to claim 1, wherein the electromagnetic wave is infrared ray, visible light or ultraviolet ray.

3. The negative pressure wound therapy system with exudate level detection through photoelectric total internal reflection according to claim 1, wherein a plurality of grades for the exudate level are set in the fluid collection canister, and each grade for the exudate level corresponds to one detecting module.

4. The negative pressure wound therapy system with exudate level detection through photoelectric total internal reflection according to claim 3, further comprising an alarming apparatus, wherein in a case that the detection control unit of the detecting module at a top grade for the exudate level determines according to a determination of whether the receiving unit receives the electromagnetic wave or ultrasonic wave signal that there exist exudates at the top grade for the exudate level, it is determined that the collection canister is full of wound exudates, and a warning trigger signal is sent to the alarming apparatus, and the alarming apparatus sends out an alarming signal.

5. The negative pressure wound therapy system with exudate level detection through photoelectric total internal reflection according to claim 1, wherein the detection control unit is adapted to control an intensity of the electromagnetic wave or ultrasonic wave transmitted by the transmitting unit.

6. The negative pressure wound therapy system with exudate level detection through photoelectric total internal reflection according to claim 1, wherein the detection control unit is adapted to control a coding rule for the electromagnetic wave or ultrasonic wave transmitted by the transmitting unit, determine whether a received code is valid and control the receiving unit whether or not to perform receiving.

7. The negative pressure wound therapy system with exudate level detection through photoelectric total internal reflection according to claim 1, wherein the amount of the detecting modules is from 2 to 10.

8. The negative pressure wound therapy system with exudate level detection through photoelectric total internal reflection according to claim 3, further comprising a display unit, wherein the display unit is arranged in the negative pressure wound therapy device and connected to the detection control unit to display the grades for the exudate level in the fluid collection canister.

9. The negative pressure wound therapy system with exudate level detection through photoelectric total internal reflection according to claim 1, wherein θ is 100 degrees.

* * * * *